United States Patent
Fernholz

(12) 
(10) Patent No.: US 6,235,509 B1
(45) Date of Patent: May 22, 2001

(54) PROCESS FOR INHIBITING SERINE PROTEASES USING CRESOL OR 3-HYDROXYPYRIDINE AND SULFONIC ACID DERIVATIVES OR FLUOROPHOSPHONATES

(75) Inventor: Erhard Fernholz, Weilheim (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/147,502

(22) PCT Filed: Jul. 10, 1997

(86) PCT No.: PCT/EP97/03668
§ 371 Date: Mar. 17, 1999
§ 102(e) Date: Mar. 17, 1999

(87) PCT Pub. No.: WO98/02533
PCT Pub. Date: Jan. 22, 1998

(30) Foreign Application Priority Data

Jul. 12, 1996  (DE) .............................. 196 28 236

(51) Int. Cl.[7] .............. C12N 9/99; C12N 9/50; C12Q 1/37; A61K 31/435

(52) U.S. Cl. ............. 435/184; 435/219; 435/23; 514/277

(58) Field of Search ................ 514/277; 435/184, 435/23, 219

(56) References Cited

PUBLICATIONS

Database Biological Abstracts, Accession No. 89:451839, N. Zolotov et al; "3–Hydroxypridine derivatives as the inhibitors of proteolytic enzymes".

M. Deutscher: "Method in Enzymology, vol. 182, Guide to protein purification" 1990.

Database Medline, Accession No. 93039690, 1992, J. Brange and L. Langkjaer: "Chemical stability of insulin 3. Influence of excipients, formulation, and pH".

"The Merck Index", 1996, Merck & Co. Whitehouse Station, NJ.

*Primary Examiner*—David M. Naff
*Assistant Examiner*—Mike Meller
(74) *Attorney, Agent, or Firm*—Arent Fox Kintner Plotkin & Kahn, PLLC

(57) ABSTRACT

A process is provided for inhibiting serine proteases in a sample. The process involves adding to the sample a compound such as cresol or 3-hydroxypyridine and then adding to the sample a sulfonic acid derivative or a fluorophosphonate, to derivative the serine proteases. The compounds such as cresol or 3-hydroxypyridine avoid non-specific derivatization of proteins other than the serine proteases.

6 Claims, 4 Drawing Sheets

Chymotrypsin inhibition with Pefabloc

Figure 1:
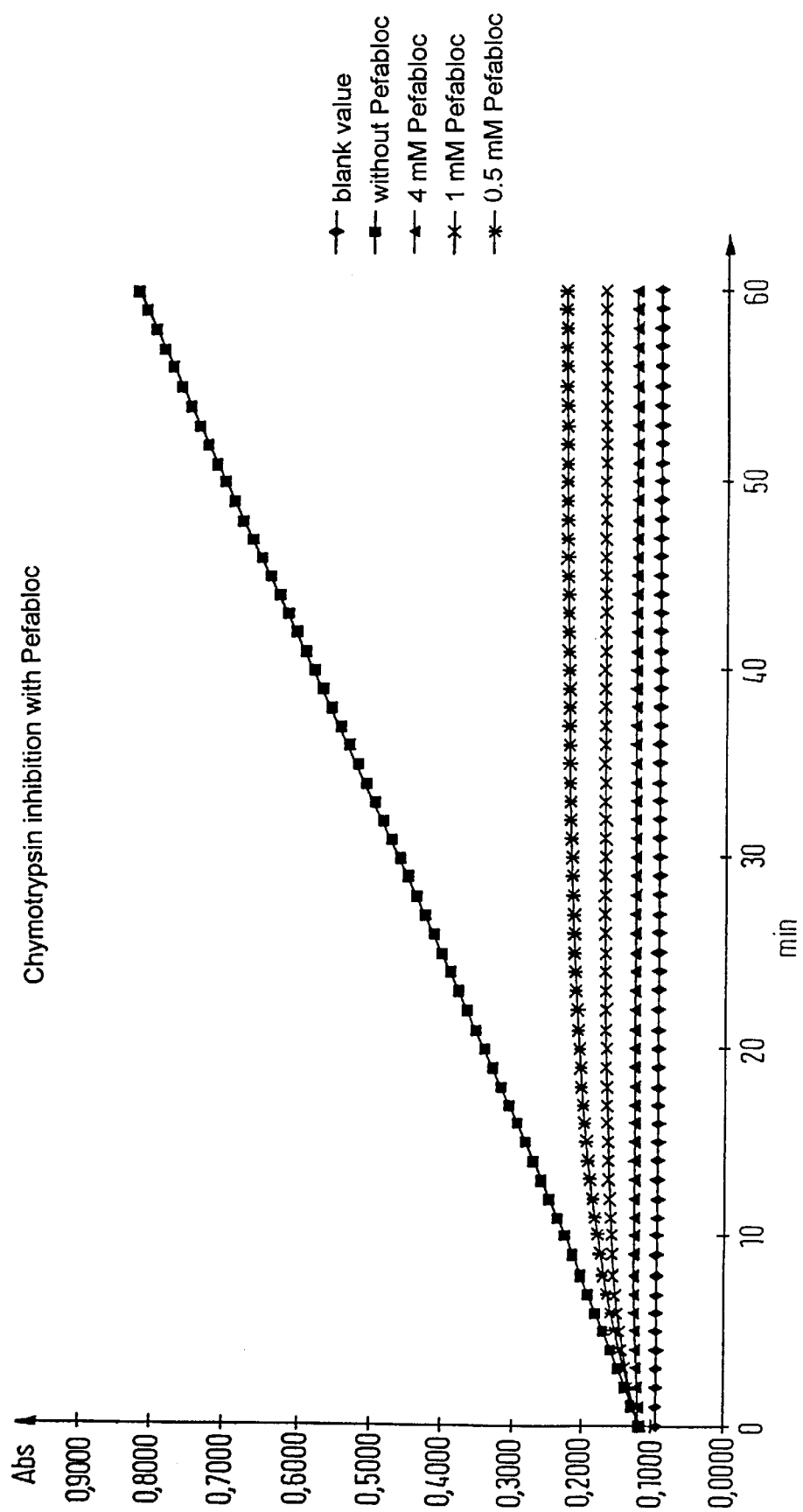

SEQUENCE LISTING

```
<160> NUMBER OF SEQ ID NOS: 1

<210> SEQ ID NO: 1
<211> LENGTH: 4
<212> TYPE: PRT
<213> ORGANISM: Artificial Sequence
<220> FEATURE:
<221> NAME/KEY: misc_feature
<222> LOCATION: (1)..(4)
<223> OTHER INFORMATION: chymotrypsin specific-substrate
<221> NAME/KEY: misc_feature
<222> LOCATION: (1)..(1)
<223> OTHER INFORMATION: Bound to succinyl
<221> NAME/KEY: misc_feature
<222> LOCATION: (4)..(4)
<223> OTHER INFORMATION: Bound to nitroanalide

<400> SEQUENCE: 1

Ala Ala Pro Phe
```

PROCESS FOR INHIBITING SERINE PROTEASES USING CRESOL OR 3-HYDROXYPYRIDINE AND SULFONIC ACID DERIVATIVES OR FLUOROPHOSPHONATES

DESCRIPTION

The present invention concerns a process for inhibiting serine proteases by derivatization with sulfonic acid derivatives or fluorophosphates, a reagent for avoiding unspecific derivatization of other proteins during the inhibition of serine proteases by sulfonic acid derivatives or fluorophosphates as well as a reagent kit for the specific inhibition of serine proteases.

The catalytically active binding pocket of serine proteases can be specifically labelled and hence inhibited by sulfonic acid derivatives, and in particular by fluorides or fluorophosphates thereof. This can, on the one hand, be used to determine the protease category (serine, cysteine, metallo, aspartyl protease) and, on the other hand, to protect proteins from proteolytic degradation (Markwardt in Pharmazie 26 (1971), 401–404, J. Kraut, Ann. Rev. Biochem. (1977), vol. 46, p. 331–358).

Although the selectivity of the reaction is very high, unspecific secondary reactions with other proteins can be occasionally detected e.g. when using the inhibitors AEBSF (4-(2-aminoethyl)-phenyl-sulfonyl fluoride), PMSF (phenylmethyl-sulfonyl fluoride), diisopropyl fluorophosphate (DFP) or amidinophenylmethylsulfonyl fluoride (APMSF). These depend above all on the pH conditions of the reaction, the protein concentration, the sulfonyl fluoride or fluorophosphate concentration and the type of accessible amino acids. Thus at high pH values, reactions can occur at the amino terminus, on lysines and on tyrosines of proteins. Such secondary reactions are of course especially undesired for proteins which are used therapeutically or diagnostically. Furthermore this can lead to falsifications of the measurement results (e.g. determination of the protein concentration by absorption at 280 nm). The secondary reactions can for example be detected by sequence analysis or simply by mass spectroscopic analyses.

Methods Enzymol. 182 (1990), p. 87, 88 and 180, 181 describes a method for detecting protease contaminations in protein preparations and mentions protease inhibitors together with information on concentration ranges in which such protease inhibitors are to be used. Processes or reagents for inhibiting an unspecific derivatization of proteins when using protease inhibitors are not disclosed.

In a further document of the prior art (Database Biol. Abs., 89: 451839) the inhibitory effect on serine proteases and in particular on trypsin and α-chymotrypsin of 2-ethyl-6-methyl-3-oxypyridine antioxidants phosphorylated on the oxy group is described. An increase in the specificity of protease inhibitors is not disclosed.

Hence the object of the present invention was to provide a method for avoiding unspecific secondary reactions when serine proteases are inhibited by sulfonic acid derivatives and fluorophosphates.

This object is achieved by a process for inhibiting serine proteases by derivatization with sulfonic acid derivatives or fluorophosphates which is characterized in that, in order to avoid unspecific derivatization of other proteins, a compound of the general formula (I)

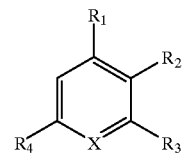

is added in which

X denotes C or N, $R_1$ denotes H, methyl, ethyl or OH, $R_2$ and $R_3$ each denote H, methyl, ethyl, OH or residues which together form a ring closure with a maximum of 6 C atoms in the ring and $R_4$ denotes H, OH or an optionally substituted alkyl, alkenyl or alkinyl group with up to 4 C atoms provided that at least one of $R_1$, $R_2$, $R_3$ or $R_4$ represents an OH group and the compound has a pKa of at least 8.

It has surprisingly turned out that the addition of compounds of formula (I) enables unspecific derivatization of proteins other than serine proteases to be practically completely prevented. The requirements which the compounds of formula (I) have to fulfill for this are primarily the stated pKa value since compounds with a lower pKa value do not adequately prevent the unspecific secondary reactions. Furthermore the optional residues on the groups $R_1$, $R_2$, $R_3$ and $R_4$ and the possible ring closure by the residues $R_2$ and $R_3$, should not allow the compound to reach a size which makes it ineffective due to steric hindrance. Attainment of the maximum size of the residues can be easily established by simple preliminary experiments. Within the scope of the present invention it is preferred to use a cresol in particular p-cresol or 3-hydroxypyridine as the compound of formula (I). Both compounds are extremely effective.

The process according to the invention is therefore preferably used to process fermentations, culture broths and cell lysates; i.e. only interfering serine proteases are irreversibly inhibited without an unspecific derivatization of the desired protein occurring. This is for example advantageous when producing proteins which are intended for therapeutic measures if the protein is obtained by genetic engineering and the cell lysate is treated with sulfonic acid derivatives or fluorophosphates to avoid loss of activity by serine proteases. The compound of the general formula (I) added in the process according to the invention has in addition a low molecular weight and can thus easily be subsequently separated during the purification e.g. by dialysis.

A further subject matter of the present invention is a reagent for avoiding unspecific derivatization of proteins when serine proteases are inhibited by sulfonic acid derivatives or fluorophosphates to which a compound of the general formula (I)

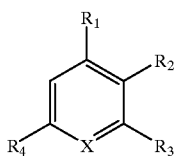

is added in which
X denotes C or N,
$R_1$ denotes H, methyl, ethyl or OH,
$R_2$ and $R_3$ each denote H, methyl, ethyl, OH or residues which together form a ring closure with a maximum of 6 C atoms in the ring and
$R_4$ denotes H, OH or an optionally substituted alkyl, alkenyl or alkinyl group with up to 4 C atoms provided that at least one of $R_1$, $R_2$, $R_3$ or $R_4$ represents an OH group and the compound has a pKa of at least 8.

In a particularly preferred embodiment the reagent according to the invention contains a cresol, in particular p-cresol, or 3-hydroxypyridine.

As already mentioned above, the reagent according to the invention can be used advantageously in the processing of fermentations and culture broths in which serine proteases are present and where it is intended to inhibit these by sulfonic acid derivatives in order to avoid losses of desired proteins.

A further subject matter of the present invention is a reagent kit which contains a) a sulfonic acid derivative or fluorophosphate and b) a compound of the general formula (I)

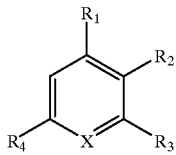

in which
X denotes C or N,
$R_1$ denotes H, methyl, ethyl or OH,
$R_2$ and $R_3$ each denote H, methyl, ethyl, OH or residues which together form a ring closure with a maximum of 6 C atoms in the ring and
$R_4$ denotes H, OH or an optionally substituted alkyl, alkenyl or alkinyl group with up to 4 C atoms provided that at least one of $R_1$, $R_2$, $R_3$ or $R_4$ represents an OH group and the compound has a pKa of at least 8.

Such a reagent kit can be used advantageously for the inhibition according to the invention of serine proteases by derivatization with sulfonic acid derivatives or fluorophosphates to avoid unspecific derivatization of other proteins. In particular interfering proteases can be irreversibly inhibited in culture broths by this means as already mentioned. It is therefore advantageous to provide a reagent kit according to the invention as a package unit in order to carry out the process according to the invention. In a particularly preferred embodiment the reagent kit according to the invention contains AEBSF, APMSF or PMSF as the sulfonic acid derivative or a fluorophosphate such as DFP and a cresol in particular or 3-hydroxy-pyridine as b). Both components of the reagent kit a) and b) must be present in separate vessels since they would otherwise already react together before carrying out the actual process and their effectiveness would suffer.

The process according to the invention, the reagent and the reagent kit enable for the first time the specific inactivation of serine proteases in protein mixtures without changing the other proteins that are present in this process. This is above all of particular interest with regard to the production of proteins by genetic engineering for diagnostic and therapeutic applications. Especially within the framework of the approval of therapeutic proteins it is of major importance whether the proteins can be obtained in a pure form. If proteins are unspecifically derivatized during the production process this can result in the corresponding pharmaceutical preparation no longer meeting the approval conditions and thus necessitating a new approval process. However, in the process according to the invention for the inhibition of serine proteases, an unspecific derivatization is substantially and in some cases even completely avoided.

The present invention is further elucidated by the examples in conjunction with the figures.

Figure 2:
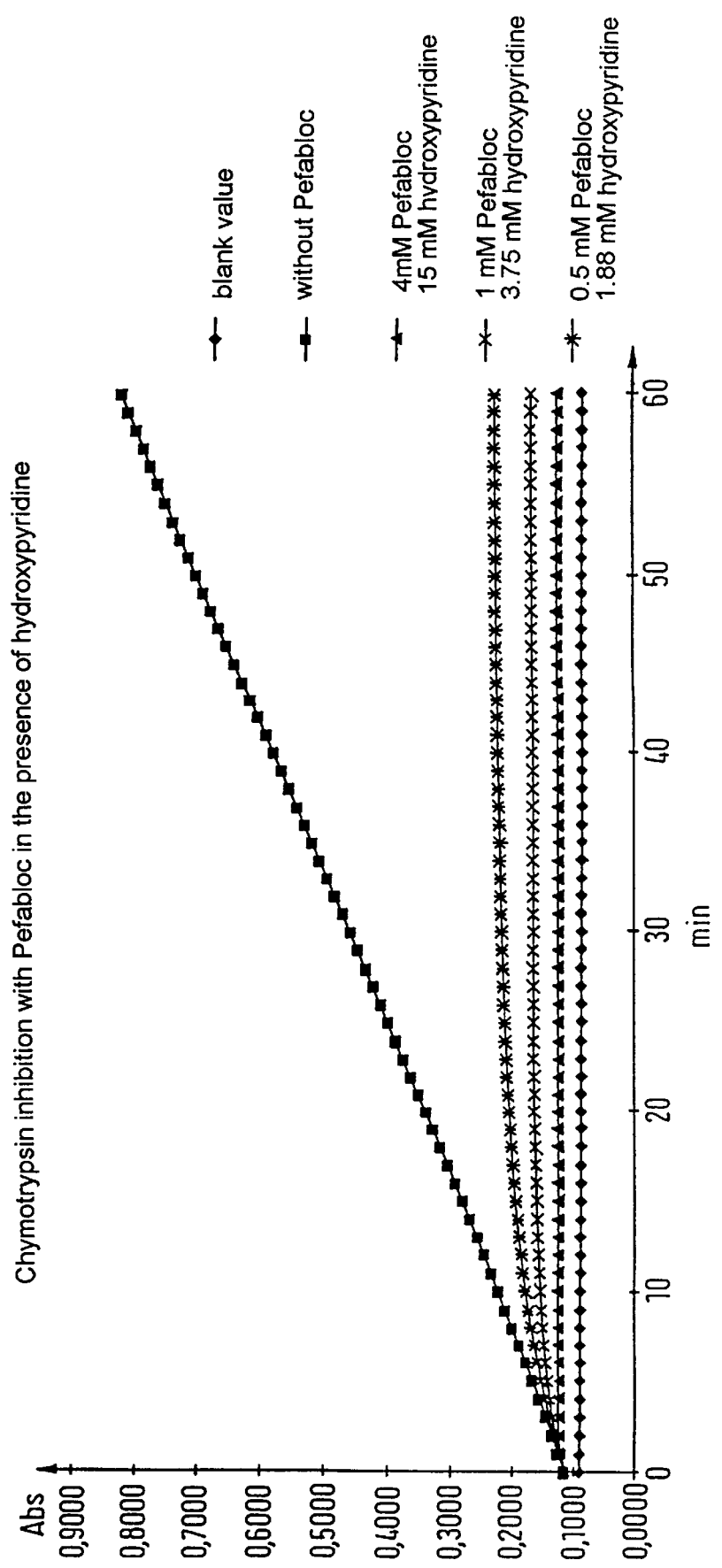
Figure 3:
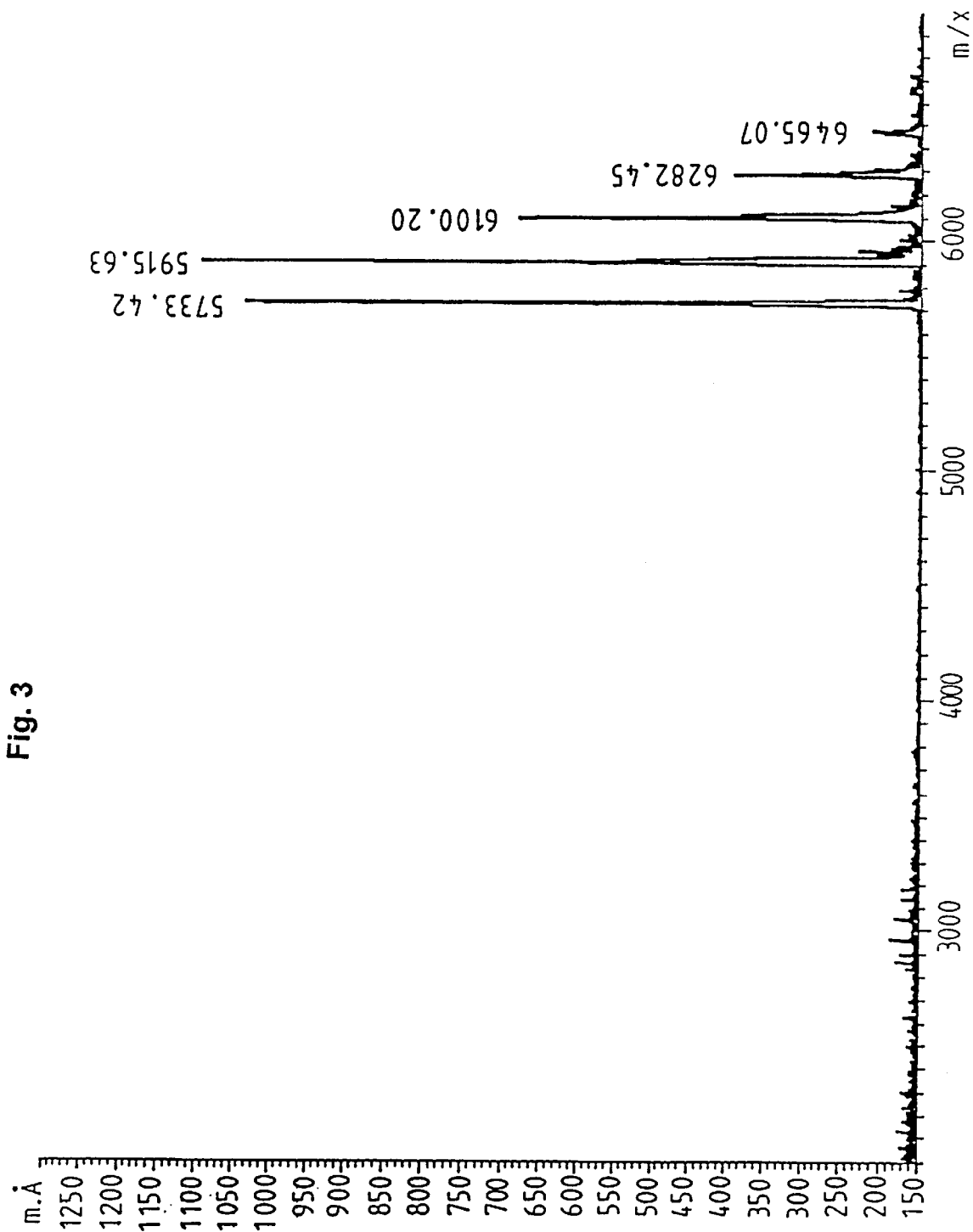
Figure 4:
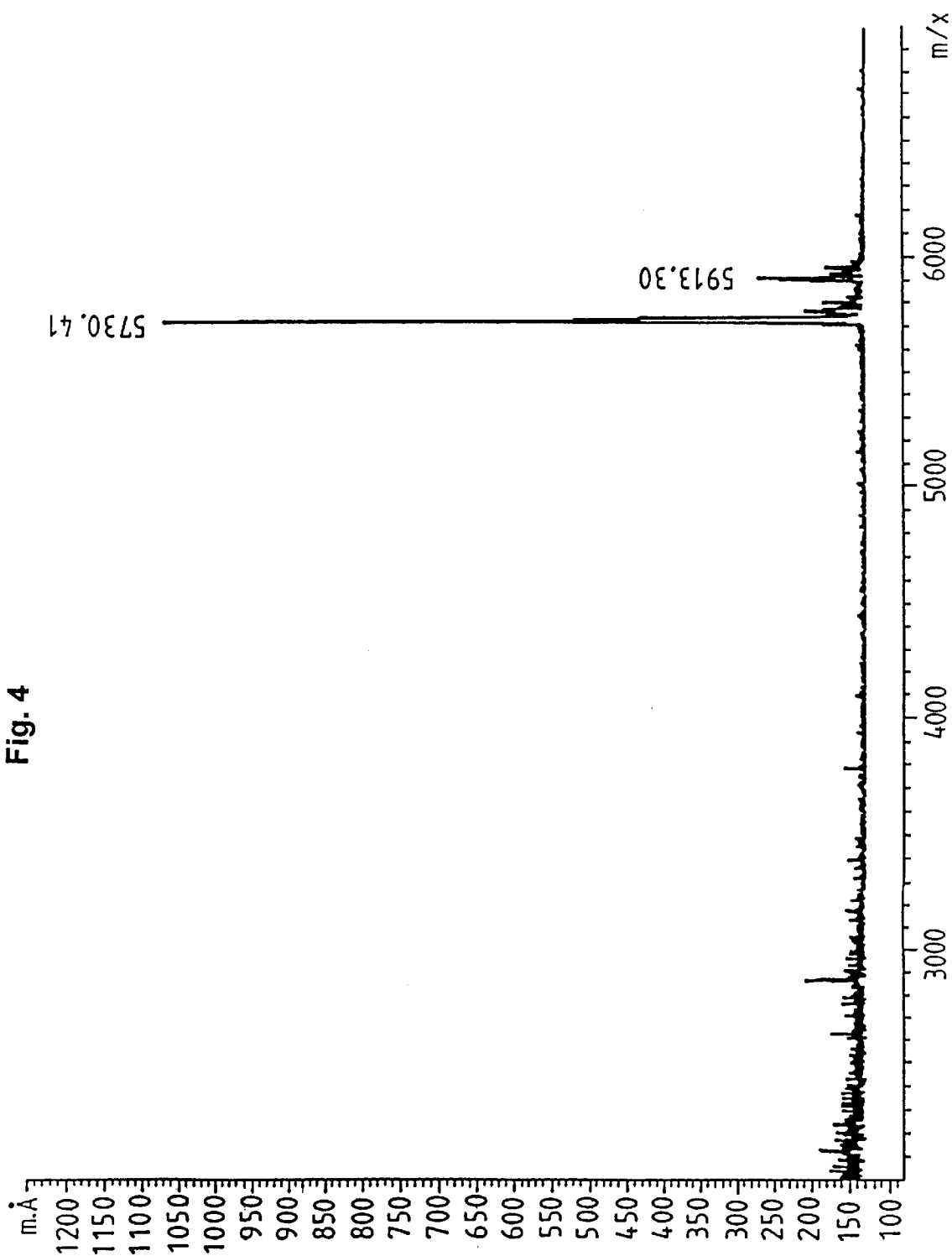

FIG. 1 shows a measurement of the activity of chymotrypsin and the inhibition of chymotrypsin when various concentrations of Pefabloc (AEBSF) are added;

FIG. 2 shows the chymotrypsin inhibition with Pefabloc (AEBSF) in the presence of hydroxypyridine; and FIGS. 3 and 4 shows MALDI-TOF spectra which were recorded of insulin treated with AEBSF with (FIG. 3) or without (FIG. 4) addition of 3-hydroxypyridine. FIG. 3 clearly shows the 4- to 5-fold unspecific derivatization of insulin on tyrosine and lysine residues with AEBSF whereas only the insulin peak and a very weak peak for single derivatization is seen in FIG. 4.

EXAMPLE 1

Monitoring the inhibition of chymotrypsin with AEBSF in the presence or absence of 3-hydroxypyridine Solution of chymotrypsin in 0.113 M Tris, 0.02 M CaCl2, pH 8.0 with or without 3-hydroxypyridine. In quick succession Suc-Ala-Ala-Pro-Phe-4-nitro-anilide was added as the substrate (0.19 mM in the test) and an AEBSF solution in 0.113M Tris, 0.02 M $CaCl_2$, pH 8.0 was added to a final concentration in the test of 4–0.5 mM. Subsequently the reaction is immediately monitored by the change of absorbance at 405 nm versus time. FIG. 1 and FIG. 2 show that the kinetics of the inhibition are not changed.

EXAMPLE 2

Reaction of insulin with AEBSF with or without 3-hydroxypyridine and monitoring of the non-specific reactions by MALDI-TOF analysis.

0.1 ml aqueous insulin solution (1 mg/ml) is added to 2.5 ml of a freshly prepared solution of 0.113 M Tris, 0.02 M $CaCl_2$, 4 mM AEBSF, 15 mM 3-hydroxypyridine, pH 8.0.

The reaction is monitored by MALDI-TOF. For this 5 μl of the reaction mixture is removed each time and mixed with 5 μl of a matrix solution (50 mM sinapic acid in 70 % acetonitrile, 0.1 % TFA) of which 2 μl is applied to the target for examination. Additional signals soon appear in the absence of 3-hydroxypyridine. In attachment 2 the reaction is shown after 21 hours reaction time. However, these secondary reactions are substantially inhibited with 3-hydroxypyridine (see FIG. 3 and 4).

What is claimed is:

1. A process for inhibiting serine proteases in a sample comprising the steps:
   (i) adding to said sample a compound of the general formula (I) and

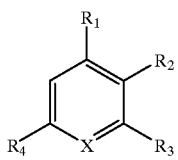

(I)

in which
X denotes C or N,
$R_1$ denotes H, methyl, ethyl or OH,
$R_2$ and $R_3$ each denote H, methyl, ethyl, OH or residues which together form a ring closure with a maximum of 6 C atoms in the ring and
$R_4$ denotes H, OH or an optionally substituted alkyl, alkenyl or alkinyl group with up to 4 C atoms provided that at least one of $R_1$, $R_2$, $R_3$ or $R_4$ represents an OH group and the compound has a pKa of at least 8 and
   (ii) adding to said sample a compound selected from the group consisting of sulfonic acid derivatives and fluorophosphonates, to derivative said serine proteases, wherein said compound (I) avoids nonspecific derivatization of proteins other than said serine proteases.

2. The process as claimed in claim 1,
wherein
a cresol or 3-hydroxypyridine is used as the compound of the general formula (I).

3. The process as claimed in claim 2,
wherein
p-cresol is used as the cresol.

4. The reagent kit for inhibiting serine proteases containing in separate vessels
   a) a sulfonic acid derivative or a fluorophosphate and
   b) a compound of the general formula (I)

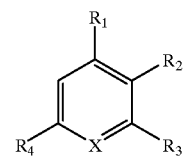

(I)

in which
x denotes C or N,
$R_1$ denotes H, methyl, ethyl or OH,
$R_2$ and $R_3$ each denote H, methyl, ethyl, OH or residues which together form a ring closure with a maximum of 6 C atoms in the ring and
$R_4$ denotes H, OH or an optionally substituted alkyl, alkenyl or alkinyl group with up to 4 C atoms provided that at least one of $R_1$, $R_2$, $R_3$ or $R_4$ represents an OH group and the compound has a pKa of at least 8.

5. The reagent kit as claimed in claim 4,
wherein
the sulfonic acid derivative or fluorophosphate is 4-(2-aminoethyl)-phenyl-sulfonyl fluoride hydrochloride, diisopropyl fluorophosphate (DFP), amidinophenylmethylsulfonyl fluoride (APMSF) or phenylmethylsulfonyl fluoride and the compound of the general formula (I) is cresol or 3-hydroxypyridine.

6. The reagent kit as claimed in claim 5,
wherein
the cresol is p-cresol.

* * * * *